(12) United States Patent
Maratos-Flier et al.

(10) Patent No.: US 7,256,176 B2
(45) Date of Patent: *Aug. 14, 2007

(54) METHODS OF MODULATING β CELL FUNCTION

(75) Inventors: Eleftheria Maratos-Flier, Newton, MA (US); Rohit N. Kulkarni, Brookline, MA (US); Pavlos Pissios, Boston, MA (US)

(73) Assignee: Joslin Diabetes Center, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/509,963

(22) Filed: Aug. 24, 2006

(65) Prior Publication Data

US 2006/0293246 A1    Dec. 28, 2006

Related U.S. Application Data

(62) Division of application No. 10/355,645, filed on Jan. 31, 2003, now Pat. No. 7,101,845.

(60) Provisional application No. 60/353,752, filed on Jan. 31, 2002.

(51) Int. Cl.
*A61K 38/00* (2006.01)
*A61K 38/28* (2006.01)
*A61K 38/04* (2006.01)

(52) U.S. Cl. .............. 514/20; 514/3; 530/30; 530/26; 530/27; 530/28; 530/29

(58) Field of Classification Search .............. 514/3, 514/20
See application file for complete search history.

(56) References Cited

U.S. PATENT DOCUMENTS

| 6,291,195 | B1 | 9/2001 | Salon et al. |
| 6,329,403 | B1 | 12/2001 | Odaka et al. |
| 7,101,845 | B2 * | 9/2006 | Maratos-Flier et al. ........ 514/3 |

OTHER PUBLICATIONS

Ozcan et al. "Melanocyte-concentrating hormone stimulates insulin release via MCH receptors expressed in islets." Jun. 14-18, 2002, abstract presented at American Diabetes Association 62nd Annual Meeting and Scientific Sessions, San Franciso.*

Audinot et al., "[125I]-S36057: a new and highly potent radioligand for the melanin-concentrating hormone receptor," Br. J. Pharmacol. 133(3):371-378 (2001).
Bednarek et al., "Synthesis and Biological Evaluation in Vitro of Selective high affinity peptide antagonists of human melanin-concentrating hormone action at human melanin-concentrating hormone receptor 1," Biochem., 41(20):6383-6390, (2002).
Boutin et al., "Melanin-concentrating hormone and its receptors: state of the art," Can. J. Physiol. Pharmacol., 80(5):388-395, (2002).
Lebl et al., "Melanin concentrating hormone analogues: contraction of the cyclic structure. 1. Agonist activity," J. Med. Chem., 31(5):949-54, (1998).
Lebl et al., "Melanin concentrating hormone analogues: contraction of the cyclic structure. II. Antagonist activity," Life Sci., 44(7):451-457, (1989).
Ludwig et al., "Melanin-concentrating hormone overexpression in transgenic mice leads to obesity and insulin resistance," J. Clin. Invest., 107(3):379-386 (2001).
Ludwig et al., "Melanin-concentrating hormone: a functional melanocortin antagonist in the hypothalamus," Am. J. Physiol. 274 (Endocrinol. Metab. 37):E627-E633, (1998).
MacDonald et al., "Molecular characterization of the melanin-concentrating hormone/receptor complex: identification of critical residues involved in binding and activation," Mol. Pharmacol., 58(1):217-225 (2000).
Matsunaga et al., "Melanin concentrating hormone (MCH): structure-function aspects of its melanocyte stimulating hormone-like (MSH-like) activity." Peptides, 10(4):773-8, (1989).
Maulon-Feraille et al., "Appetite-boosting property of pro-melanin-concentrating hormone(131-165) (neuropeptide-glutamic acid-isoleucine) is associated with proteolytic resistance." J. Pharmacol. Exp. Ther. 302(2):766-773, (2002).
Ozcan et al., "Melanocyte-concentrating hormone stimulates insulin release via MCH receptors expressed in islets," Jun. 14-18, 2002, abstract presented at American Diabetes Association 62nd Annual Meeting and Scientific Sessions, San Francisco.
Rossi et al., "Melanin-concentrating hormone acutely stimulates feeding, but chronic administration has no effect on body weight," Endocrinology, 138(1):351-355, (1997).
Tritos et al., "Characterization of expression of hypothalamic appetite-regulating peptides in obese hyperleptinemic brown adipose tissue-deficient (uncoupling protein-promoter-driven diphtheria toxin A) mice," Endocrinology, 139(11):4634-4641, (1998).
Vitale et al., "Conformational features of human melanin-concentrating hormone: an NMR and computational analysis," Chembiochem., 4(1):73-81 (2003).

* cited by examiner

*Primary Examiner*—Ceclilia J. Tsang
*Assistant Examiner*—Maury Audet
(74) *Attorney, Agent, or Firm*—Fish & Richardson P.C.

(57) ABSTRACT

Methods of modulating pancreatic function by modulating MCH signaling in a β cell.

17 Claims, No Drawings

```
                         SEQUENCE LISTING

<160> NUMBER OF SEQ ID NOS: 7

<210> SEQ ID NO 1
<211> LENGTH: 19
<212> TYPE: PRT
<213> ORGANISM: Homo sapiens

<400> SEQUENCE: 1

Asp Phe Asp Met Leu Arg Cys Met Leu Gly Arg Val Tyr Arg Pro Cys
 1               5                  10                  15

Trp Gln Val

<210> SEQ ID NO 2
<211> LENGTH: 11
<212> TYPE: PRT
<213> ORGANISM: Artificial Sequence
<220> FEATURE:
<223> OTHER INFORMATION: synthetically generated peptide (Ac-hMCH(6-16))
<220> FEATURE:
<221> NAME/KEY: DISULFID
<222> LOCATION: 2, 11
<223> OTHER INFORMATION: Disulfide bond Cys(2)-Cys(11)

<400> SEQUENCE: 2

Arg Cys Met Leu Gly Arg Val Tyr Arg Pro Cys
 1               5                  10

<210> SEQ ID NO 3
<211> LENGTH: 11
<212> TYPE: PRT
<213> ORGANISM: Artificial Sequence
<220> FEATURE:
<223> OTHER INFORMATION: synthetically generated peptide (Ac-dArg(6)-
      hMCH(6-16))
<220> FEATURE:
<221> NAME/KEY: VARIANT
<222> LOCATION: 1
<223> OTHER INFORMATION: Xaa = D-amino acid, D-Arg
<220> FEATURE:
<221> NAME/KEY: DISULFID
<222> LOCATION: 2, 11
<223> OTHER INFORMATION: Disulfide bond Cys(2)-Cys(11)

<400> SEQUENCE: 3

Xaa Cys Met Leu Asn Arg Val Tyr Arg Pro Cys
 1               5                  10

<210> SEQ ID NO 4
```

```
-continued

<211> LENGTH: 5
<212> TYPE: PRT
<213> ORGANISM: Artificial Sequence
<220> FEATURE:
<223> OTHER INFORMATION: fragment of human MCH

<400> SEQUENCE: 4

Val Tyr Arg Pro Cys
 1               5

<210> SEQ ID NO 5
<211> LENGTH: 4
<212> TYPE: PRT
<213> ORGANISM: Artificial Sequence
<220> FEATURE:
<223> OTHER INFORMATION: fragment of human MCH

<400> SEQUENCE: 5

Tyr Arg Pro Cys
 1

<210> SEQ ID NO 6
<211> LENGTH: 35
<212> TYPE: PRT
<213> ORGANISM: Homo sapiens

<400> SEQUENCE: 6

Arg Glu Ile Gly Asp Glu Glu Ser Ala Lys Phe Pro Ile Gly Arg Arg
 1               5                  10                  15

Asp Phe Asp Met Leu Arg Cys Met Leu Gly Arg Val Tyr Arg Pro Cys
                20                  25                  30

Trp Gln Val
         35

<210> SEQ ID NO 7
<211> LENGTH: 14
<212> TYPE: PRT
<213> ORGANISM: Artificial Sequence
<220> FEATURE:
<223> OTHER INFORMATION: synthetically generated peptide (S36057)
<220> FEATURE:
<221> NAME/KEY: VARIANT
<222> LOCATION: 2
<223> OTHER INFORMATION: Xaa = 8-amino-3,6-dioxaoctanol

<400> SEQUENCE: 7

Tyr Xaa Arg Cys Met Leu Gly Arg Val Phe Arg Pro Cys Trp
 1               5                  10
```

METHODS OF MODULATING β CELL FUNCTION

RELATED APPLICATIONS

This application is a divisional of U.S. patent application Ser. No. 10/355,645, filed Jan. 31, 2003, which claims the benefit of U.S. Provisional Application No. 60/353,752, filed Jan. 31, 2002. The contents of both applications are incorporated herein by reference.

GOVERNMENT RIGHTS

This invention was made with U.S. government support under grant numbers DK 56113, 56116, and 09825 awarded by the National Institutes of Health. The government has certain rights in the invention.

BACKGROUND

Melanocyte concentrating hormone (MCH) is a cyclic 19 amino-acid peptide that is an important regulator of feeding behavior. In the brain, MCH is synthesized in neurons of the lateral hypothalamus, which make monosynaptic connections throughout the cortex. MCH neurons also synapse with neurons in the parabrachial nucleus and the nucleus of the tractus solitarius, hindbrain nuclei important in ingestive behavior.

MCH has been shown to circulate in plasma and to stimulate leptin secretion from rat adipocytes. When administered ICV, MCH induces an acute increase in feeding. Mice in which the MCH gene has been ablated are hypophagic and lean.

SUMMARY OF THE INVENTION

The invention is based, in part, on the inventors' discovery that MCH modulates pancreatic endocrine function, e.g., β-cell function, e.g., insulin secretion. While not being bound by theory, MCH is thought to stimulate insulin release from islet β-cells directly via the MCH receptor. In addition, MCH is believed to act as a growth factor for islet cells.

Accordingly, the invention features a method of modulating pancreatic function, e.g., β cell function, e.g., insulin secretion or β cell size or growth. The method includes modulating MCH signaling in a β cell. In a preferred embodiment, the method includes administering to a β cell an agent that modulates, e.g., increases or decreases, MCH signaling in the β cell. Increasing MCH signaling can lead to increased insulin secretion, while inhibiting MCH signaling can lead to decreased insulin secretion.

In one embodiment, the agent promotes, increases or mimics MCH signaling in a β cell, to thereby increase insulin release from the β cell, or increase β cell size or growth. In one embodiment, the agent promotes, increases or mimics MCH signaling by binding to a protein on the surface of the β cell, e.g., MCH receptor, e.g., MCH-R1 or MCH-R2, and, e.g., agonizes or mimics MCH binding. An agent that promotes, increases or mimics MCH signaling can be one or more of: an MCH peptide or a functional analog thereof (e.g., [Ala-14]-MCH); an MCH receptor (MCH-R) polypeptide or functional variant or analog thereof; a peptide or protein agonist of MCH-R, e.g., a protein or peptide that activates the MCH receptor; a small molecule that increases expression of MCH or MCH-R, e.g., by binding to the promoter region of the MCH or MCH-R gene; an antibody, e.g., an antibody or antigen binding fragment thereof that binds to MCH or MCH-R and, e.g., activates MCH-R or stabilizes the binding of MCH to MCH-R or of MCH-R to a secondary messenger, e.g., a G protein, e.g., $G_i$; or a nucleotide sequence encoding an MCH or MCH-R polypeptide or functional fragment or analog thereof. The nucleotide sequence can be a genomic sequence or a cDNA sequence. The nucleotide sequence can include: an MCH or MCH-R coding region; a promoter sequence, e.g., a promoter sequence from an MCH or MCH-R gene or from another gene; an enhancer sequence; untranslated regulatory sequences, e.g., a 5' untranslated region (UTR), e.g., a 5'UTR from an MCH or MCH-R gene or from another gene, a 3' UTR, e.g., a 3'UTR from an MCH or MCH-R gene or from another gene; a polyadenylation site; an insulator sequence. In another preferred embodiment, the level of an MCH or MCH-R protein is increased by increasing the level of expression of an endogenous MCH or MCH-R gene, e.g., by increasing transcription of the MCH or MCH-R gene or increasing MCH or MCH-R mRNA stability. In a preferred embodiment, transcription of the MCH or MCH-R gene is increased by: altering the regulatory sequence of the endogenous MCH or MCH-R gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the MCH or MCH-R gene to be transcribed more efficiently.

In a preferred embodiment, an agent that promotes, increases or mimics MCH signaling is an MCH agonist selected from: MCH and analogs thereof, including Arg-cyclo(S-S)(Cys-Met-Leu-Gly-Arg-Val-Tyr-Arg-Pro-Cys (SEQ ID NO:2)) (Bednarek et al. (2001) Biochemistry 40(31):9379-86)); pro-MCH(131-165) peptide known as neuropeptide-glutamic acid-isoleucine (NEI)-MCH (Maulon-Feraille (2002) J Pharmacol Exp Ther 302(2):766-73; Ac-REIGDEESAKFPIGRRDFDMLRCM-LGRVYRPCWQV (SEQ ID NO:6)); Ac-dArg(6)-cyclo(S-S)(Cys(7)-Met(8)-Leu(9)-Asn(10)-Arg(11)-Val(12)-Tyr (13)-Arg(14)-Pro(15)-Cys(16))-NH(2) (SEQ ID NO:3) (Bednarek et al. (2002) J Biol Chem 277(16):13821-6); and compound S36057 (Audinot et al. (2001) Br J Pharmacol 133(3):371-8; Y-ADO-RCMLGRVFRPCW (SEQ ID NO:7; ADO is 8-amino-3,6-dioxyoctanol). Other agonists are known or can be readily identified using routine techniques.

In another embodiment, the agent decreases or inhibits MCH signaling, to thereby decrease insulin secretion or decrease islet cell growth. In one embodiment, the agent decreases or inhibits MCH signaling by binding to a protein on the surface of the β cell, e.g., MCH receptor, e.g., MCH-R1 or MCH-R2, and, e.g., inhibits MCH binding. An agent that decreases or inhibits MCH signaling can be one more of: an MCH or MCH-R antagonist (e.g., a [D-Arg$^{11}$]-MCH); a soluble MCH binding protein, e.g., a soluble MCH binding protein that binds to MCH and inhibits MCH binding to MCH-R or MCH-R binding to a secondary messenger, e.g., a G protein, e.g., $G_i$; a soluble MCH-R binding protein, e.g., a soluble MCH-R binding protein that binds to MCH-R and inhibits MCH-R binding to MCH; an antibody or antigen binding fragment thereof that specifically binds to MCH or MCH-R, e.g., an antibody that disrupts MCH binding to MCH-R; a mutated inactive MCH-R (e.g., an Asp-123-substituted MCH-R mutant) that, e.g., does not bind to MCH, or binds to MCH but disrupts an intracellular receptor signaling activity; an MCH or MCH-R nucleic acid molecule that can bind to a cellular MCH or MCH-R nucleic acid sequence, e.g., mRNA, and inhibit expression of the protein, e.g., an antisense molecule or MCH or MCH-R ribozyme; an agent which decreases MCH or MCH-R gene expression, e.g., a small molecule which binds the promoter of MCH or MCH-R and decreases MCH or MCH-R gene expression. In another preferred embodiment, MCH or MCH-R is inhibited by decreasing the level of expression of an endogenous MCH or MCH-R gene, e.g., by decreasing transcription of the MCH or MCH-R gene. In a preferred embodiment, transcription of the MCH or MCH-R gene can be decreased by: altering the regulatory sequences of the endogenous MCH or MCH-R gene, e.g., by the addition of a negative regulatory sequence (such as a DNA-biding site for a transcriptional repressor), or by the removal of a positive regulatory sequence (such as an enhancer or a DNA-binding site for a transcriptional activator).

In a preferred embodiment, an agent that decreases or inhibits MCH signaling is an MCH antagonist selected from: SNAP-7941 (Borowsky et al. (2002) Nat Med 8(8):825-30); Leu(9)-Gly(10) and Arg(14)-Pro(15) peptide analogs (Bednarek et al. (2002) Biochemistry 41(20):6383-90); T-226296 (Takekawa et al. (2002) Eur J Pharmacol 438(3): 129-35); MCH analogs substituted in MCH-(6-17) in 6 out of 12 amino acids with concomitant replacement of the disulfide bond by an amide bond (Audinot et al. (2001) J Biol Chem 276(17):13554-62); [D-Arg(11)]-MCH (Macdonald et al. (2000) Mol Pharmacol 58(1):217-25); and amide derivatives of 1,4-di-substituted piperidine antagonists (U.S. Pat. No. 6,472,394). Other antagonists are known or can be readily identified using routine techniques.

In a preferred embodiment, the MCH-R is MCH-R1.

In a preferred embodiment, the MCH-R is MCH-R2.

In a preferred embodiment, the agent is administered to the cell in vitro, e.g., the agent is administered to a cultured β cell. In some embodiments, the cell can subsequently be implanted into a subject. Preferred cells used in this method are autologous cells. Allogenic or xenogenic cells can also be used.

In a preferred embodiment, the agent is administered ex-vivo, e.g., the agent is administered to an isolated pancreatic tissue, e.g., an islet or islet equivalent.

In a preferred embodiment, the agent is administered in-vivo, e.g., the agent is administered to a subject. In one embodiment, the animal is an experimental animal, e.g., a rodent model for an insulin related disorder, e.g., a NOD Mouse and its related strains, BB Rat, Leptin or Leptin Receptor mutant rodents, Zucker Diabetic Fatty (ZDF) Rat, Sprague-Dawley rats, Obese Spontaneously Hypertensive Rat (SHROB, Koletsky Rat), Wistar Fatty Rat, New Zealand Obese Mouse, NSY Mouse, Goto-Kakizaki Rat, OLETF Rat, JCR:LA-cp Rat, Neonatally Streptozotocin-Induced (n-STZ) Diabetic Rats, Rhesus Monkey, Psammomys obesus (fat sand rat), C57B1/6J Mouse. In another embodiment, the subject is a human.

In a preferred embodiment, the subject is at risk for, or has, an insulin-related disorder, e.g., diabetes, e.g., type 1 or type 2 diabetes; obesity; insulin resistance; hyperinsulinemia; hypoglycemia.

In another aspect, the invention features a method of modulating pancreatic function, e.g., islet function, e.g., insulin secretion, in a subject. The method includes: providing a pancreatic cell, e.g., an islet cell, e.g., a β cell; administering to the cell an agent that modulates MCH signaling, e.g., an agent described herein; and implanting the cell into the subject. Preferred cells used in this method are cells autologous to the subject. Allogenic or xenogenic cells can also be used.

In a preferred embodiment, the agent is a nucleic acid that encodes an MCH-R, e.g., MCH-R1, MCH-R2, SLT or its rodent equivalent.

In another aspect, the invention features a method of treating a subject, e.g., treating an insulin related disorder, e.g., diabetes, e.g., type 1 or type 2 diabetes; obesity; insulin resistance; hyperinsulinemia; hypoglycemia. The method includes (a) optionally, identifying a subject having or at risk for an insulin related disorder, e.g., an insulin related disorder described herein; and (b) modulating MCH signaling to thereby treat the subject. Modulating MCH signaling modulates insulin secretion in the subject. In preferred embodiments, the method includes administering to the subject an agent that modulates MCH signaling.

In one embodiment, the agent promotes, increases or mimics MCH signaling in a β cell, to thereby increase insulin release from the β cell. In one embodiment, the agent promotes, increases or mimics MCH signaling by binding to a protein on the surface of the β cell, e.g., MCH receptor, e.g., MCH-R1 or MCH-R2, and, e.g., agonizes or mimics MCH binding. An agent that promotes, increases or mimics MCH signaling can be one or more of: an MCH peptide or a functional fragment or analog thereof (e.g., [Ala-14]-MCH); an MCH receptor (MCH-R) polypeptide or functional variant or analog thereof; a peptide or protein agonist of MCH-R, e.g., a protein or peptide that activates MCH-R signaling to increase insulin secretion activity, of MCH; a small molecule that increases expression of MCH or MCH-R, e.g., by binding to the promoter region of the MCH or MCH-R gene; an antibody, e.g., an antibody or antigen binding fragment thereof that binds to and stabilizes or assists the binding of MCH to MCH-R or of MCH-R to a secondary messenger, e.g., a G protein, e.g., $G_i$ or $G_o$; or a nucleotide sequence encoding an MCH or MCH-R polypeptide or functional fragment or analog thereof. The nucleotide sequence can be a genomic sequence or a cDNA sequence. The nucleotide sequence can include: an MCH or MCH-R coding region; a promoter sequence, e.g., a promoter sequence from an MCH or MCH-R gene or from another gene; an enhancer sequence; untranslated regulatory sequences, e.g., a 5' untranslated region (UTR), e.g., a 5'UTR from an MCH or MCH-R gene or from another gene, a 3' UTR, e.g., a 3'UTR from an MCH or MCH-R gene or from another gene; a polyadenylation site; an insulator sequence. In another preferred embodiment, the level of an MCH or MCH-R protein is increased by increasing the level of expression of an endogenous MCH or MCH-R gene, e.g., by increasing transcription of the MCH or MCH-R gene or increasing MCH or MCH-R mRNA stability. In a preferred embodiment, transcription of the MCH or MCH-R gene is increased by: altering the regulatory sequence of the endogenous MCH or MCH-R gene, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the MCH or MCH-R gene to be transcribed more efficiently.

In another embodiment, the agent decreases or inhibits MCH signaling. In one embodiment, the agent decreases or inhibits MCH signaling by binding to a protein on the surface of the β cell, e.g., MCH receptor, e.g., MCH-R1 or SLC-1, and, e.g., inhibits MCH binding. An agent that decreases or inhibits MCH signaling can be one more of: an MCH or MCH-R antagonist (e.g., a [D-Arg$^{11}$]-MCH); a soluble MCH binding protein, e.g., a soluble MCH binding protein that binds to MCH and inhibits MCH binding to MCH-R; a soluble MCH-R binding protein, e.g., a soluble MCH-R binding protein that binds to MCH-R and inhibits MCH-R binding to MCH or MCH-R binding to a secondary messenger, e.g., a G protein, e.g., $G_i$ or $G_o$; an antibody or antigen binding fragment thereof that specifically binds to MCH or MCH-R, e.g., an antibody that disrupts MCH binding to MCH-R; a mutated inactive MCH-R (e.g., an Asp-123-substituted MCH-R mutant) that, e.g., does not bind to MCH, or binds to MCH but disrupts an intracellular receptor signaling activity; an MCH or MCH-R nucleic acid molecule that can bind to a cellular MCH or MCH-R nucleic acid sequence, e.g., mRNA, and inhibit expression of the protein, e.g., an antisense molecule or MCH or MCH-R ribozyme; an agent which decreases MCH or MCH-R gene expression, e.g., a small molecule which binds the promoter of MCH or MCH-R and decreases MCH or MCH-R gene expression. In another preferred embodiment, MCH or MCH-R is inhibited by decreasing the level of expression of an endogenous MCH or MCH-R gene, e.g., by decreasing transcription of the MCH or MCH-R gene. In a preferred embodiment, transcription of the MCH or MCH-R gene can be decreased by: altering the regulatory sequences of the endogenous MCH or MCH-R gene, e.g., by the addition of a negative regulatory sequence (such as a DNA-biding site for a transcriptional repressor), or by the removal of a positive regulatory sequence (such as an enhancer or a DNA-binding site for a transcriptional activator).

In a preferred embodiment, the administration of the agent can be initiated, e.g., (a) before a subject, e.g., a subject who is at risk for an insulin relate disorder, shows clinical symptoms of an insulin related disorder; (b) after the subject begins to show signs of an insulin related disorder, e.g., elevated glucose levels or β cell failure (as evidenced, e.g., by an increase or decrease of more than 5, 10, 20, or 30% in glucose levels or β cell failure compared to a reference value, e.g., a control, e.g., a non-disease state control); (c) when an insulin related disease, e.g., diabetes or another insulin related disorder described herein is diagnosed; (d) before, during or after a treatment for an insulin related disorder, e.g., diabetes, is begun or begins to exert its effects. The period over which the agent is administered (or the period over which clinically effective levels are maintained in the subject) can be long term, e.g., for six months or more or a year or more, or short term, e.g., for less than a year, six months, one month, two weeks or less.

In a preferred embodiment, the agent is administered before the subject shows clinical symptoms of an insulin related disorder, but after a determination that the subject is at risk for an insulin related disorder, e.g., the subject is obese, or the subject has a family history of insulin related disorder (e.g., a parent, sibling or grandparent of the subject has an insulin related disorder).

In a preferred embodiment, the agent is administered in the early stages of onset of clinical symptoms of an insulin related disorder, e.g., diabetes, e.g., type 2 diabetes. For example, the agent is administered when the subject begins to show elevated glucose levels or increased β cell dysfunction, but before complete β cell failure.

In a preferred embodiment, the agent is administered as a supplemental therapy for an insulin related disorder, e.g., the agent is administered in addition to administration of insulin.

In a preferred embodiment, the subject exhibits abnormal pancreatic function, e.g., abnormal insulin secretion, e.g., the subject has an insulin related disorder, e.g., diabetes, e.g., type 1 or type 2 diabetes; obesity; insulin resistance; hyperinsulinemia; hypoglycemia.

In a preferred embodiment, a pharmaceutical composition including one or more of the agents described herein is administered in a pharmaceutically effective dose.

In a preferred embodiment, a pharmaceutical composition including one or more of the agents described herein is administered in a therapeutically effective dose.

In a preferred embodiment, the subject is a non-human animal, e.g., an animal model of an insulin related disorder, e.g., the NOD Mouse and its related strains, BB Rat, Leptin or Leptin Receptor mutant rodents, Zucker Diabetic Fatty (ZDF) Rat, Sprague-Dawley rats, Obese Spontaneously Hypertensive Rat (SHROB, Koletsky Rat), Wistar Fatty Rat, New Zealand Obese Mouse, NSY Mouse, Goto-Kakizaki Rat, OLETF Rat, JCR:LA-cp Rat, Neonatally Streptozotocin-Induced (n-STZ) Diabetic Rats, Rhesus Monkey, *Psammomys obesus* (fat sand rat), C57B1/6J Mouse.

In a preferred embodiment, the subject is a mammal, e.g., a human.

In a preferred embodiment, the subject is at risk for or has an insulin related disorder, e.g., an insulin related disorder described herein.

In a preferred embodiment, the method also includes evaluating the subject for one or more of the following parameters: (1) insulin levels; (2) glucose levels; (3) weight; (4) endogenous MCH levels or activity; (5) endogenous MCH receptor (MCH-R) levels or activity.

In another aspect, the invention features a method of culturing or propagating an islet cell or β cell preparation. The method includes culturing an islet cell or β cell preparation in the presence of MCH or an agent that increases or promotes MCH signaling, e.g., an agent that increases or promotes MCH signaling described herein, e.g., an MCH agonist. While not bound by theory, it is believed that MCH can act as a growth factor for islet/β cells. In some embodiments, the islet cell or β cell preparation includes a nucleic acid encoding an MCH-R, e.g., MCH-R1, MCH-R2, SLT, or a functional fragment thereof.

In another aspect, the invention features a method of evaluating a subject, e.g., determining if a subject is at risk for, or has, an insulin related disorder, e.g., an insulin related disorder described herein. The method includes evaluating MCH signaling in a cell or tissue, preferably in the pancreas, islets, or β-cells, of the subject. Abnormal or aberrant MCH signaling as compared to a control can indicate the risk or presence of an insulin related disorder, e.g., an insulin related disorder described herein. The method can include providing a record, e.g., a print or computer readable material, e.g., an informational, diagnostic, or instructional material, e.g., to the subject, health care provider, or insurance company, identifying the abnormal or aberrant MCH signaling as a risk or diagnostic factor for an insulin related disorder, e.g., an insulin related disorder described herein.

In a preferred embodiment, the method includes detecting a genetic lesion or mutation in a gene involved in MCH signaling, in an MCH or MCH-R gene. The human MCH peptide gene sequence is available at, e.g., Genbank Accession No. AI224977. The sequence of at least several human MCH receptors (e.g., MCH-R1 and MCH-R2) is known, and is described, e.g., in Genbank Accession Nos. AF347063 and AF347063.

In a preferred embodiment, the method includes evaluating the level of expression of a gene involved in MCH signaling, e.g., in an MCH or MCH-R gene, e.g., evaluating the amount or half life of an MCH or MCH-R mRNA. Over- or under-expression of a gene, compared to a control, can be evaluated by, e.g., Northern blot, TaqMan assay, or other methods known in the art.

In a preferred embodiment, the method includes evaluating an MCH signaling activity, e.g., MCH to MCH-R binding; or MCH-mediated insulin secretion from β cells.

In a preferred embodiment, the method includes evaluating protein levels of a protein involved in MCH signaling, e.g., levels of MCH-R, e.g., SLC-1, in a β cell.

In a preferred embodiment, the method includes treating the subject for the disorder.

In a preferred embodiment, the subject is further evaluated for one or more of the following parameters: (1) insulin levels; (2) glucose levels; (3) weight; (4) endogenous MCH levels or activity; (5) endogenous MCH receptor (MCH-R) levels or activity.

In a preferred embodiment, the evaluation is used to choose a course of treatment.

Methods of the invention can be used prenatally or to determine if a subject's offspring will be at risk for a disorder.

In another aspect, the invention features a method of evaluating an agent, e.g., screening for an agent that modulates pancreatic function, e.g., β cell function, e.g., insulin secretion. The method includes (a) providing a test agent, (b) determining if the agent modulates MCH signaling, e.g., interacts with a molecule involved in MCH signaling, e.g., MCH or MCH-R, e.g., binds to and/or modulates the levels, expression, or activity of MCH or MCH-R; and (c) correlating the ability of a test agent to modulate MCH signaling with the ability to modulate pancreatic function (e.g., insulin production or secretion). Correlating means identifying a test agent that modulates MCH signaling an agent capable of modulating pancreatic function, e.g., providing a record, e.g., a print or computer readable record, such as a laboratory record or dataset, identifying a test agent that modulates MCH signaling as an agent capable of modulating pancreatic function, e.g., insulin production or secretion. The record can include other information, such as a specific test agent identifier, a date, an operator of the method, or information about the source, structure, method of purification or biological activity of the test agent. The record or information derived from the record can be used, e.g., to identify the test agent as a compound or lead compound for pharmaceutical or therapeutic use. Agents, e.g., compounds, identified by this method can be used, e.g., in the treatment of an insulin related disorder, e.g., an insulin related disorder described herein.

In one embodiment, the method includes: providing an MCH or MCH-R protein or nucleic acid or a functional fragment thereof; contacting the MCH or MCH-R protein or nucleic acid with a test agent, and determining if the test compound interacts with, e.g., binds, the MCH or MCH-R protein or nucleic acid.

In one embodiment, the test agent binds to the MCH or MCH-R protein and modulates a MCH signaling activity. For example, the compound binds to the MCH or MCH-R protein and facilitates or inhibits any of: MCH binding to its receptor; intracellular MCH-R signaling, e.g., MCH-R binding to a second messenger; insulin secretion. Methods for assaying MCH signaling, e.g., MCH activity, e.g., methods described herein, are art-recognized.

In a preferred embodiment, the test compound is one or more of: a protein or peptide; an antibody or antigen-binding fragment thereof; a small molecule; a nucleotide sequence. For example, the agent can be an agent identified through a library screen described herein.

In a preferred embodiment, the contacting step is performed in vitro.

In another preferred embodiment, the contacting step is performed in vivo.

In a preferred embodiment, the method further includes administering the test compound to an experimental animal, e.g., an animal model for an insulin related disorder, e.g., an animal model disclosed herein.

In another embodiment, the method includes: providing a test cell, tissue, or subject; administering a test agent to the cell, tissue, or subject; and determining whether the test agent modulates MCH signaling in the cell, tissue, or subject. An agent that is found to modulate, e.g., MCH or MCH-R in the cell, tissue, or subject is identified as an agent that can modulate pancreatic function, e.g., islet or β cell function, e.g., insulin secretion.

In a preferred embodiment, the cell is a β cell.

In a preferred embodiment, the MCH-R is a human MCH-R, e.g., MCH-R1 or MCH-R2.

In a preferred embodiment, the tissue is pancreatic tissue, e.g., an islet or islet equivalent.

In a preferred embodiment, the method includes (a) providing a cell-free expression system, cell, tissue, or animal having a transgene which includes a nucleic acid that encodes a reporter molecule functionally linked to the control region, e.g., a promoter, of a gene encoding a MCH or MCH-R, e.g., an MCH-R described herein; (b) contacting the cell-free expression system, cell, tissue, or animal with a test agent; and (c) evaluating a signal produced by the reporter molecule. A test agent that causes the modulation of reporter molecule expression, compared to a reference, e.g., a negative control, is identified as an agent that can modulate pancreatic function, e.g., insulin function, e.g., insulin secretion.

In a preferred embodiment, the reporter molecule is any of: green fluorescent protein (GFP); enhanced GFP (EGFP); luciferase; chloramphenicol acetyl transferase (CAT); β-galactosidase; β-lactamase; or secreted placental alkaline phosphatase. Other reporter molecules, e.g., other enzymes whose function can be detected by appropriate chromogenic or fluorogenic substrates are known to those skilled in the art.

In a preferred embodiment, the agent is further tested in a cell-based and/or animal based model e.g., a cell based or animal model described herein.

In another aspect, the invention features a computer readable record encoded with (a) a subject identifier, e.g., a patient identifier, (b) one or more results from an evaluation of the subject, e.g., a diagnostic evaluation described herein, e.g., the level of expression, level or activity of MCH or MCH-R, in the subject, and optionally (c) a value for or related to a disease state, e.g., a value correlated with disease status or risk with regard to an insulin related disorder, e.g., an insulin related disorder described herein. In one embodiment, the invention features a computer medium having a plurality of digitally encoded data records. Each data record includes a value representing the level of expression, level or activity of MCH signaling, e.g., MCH or MCH-R levels or activity, in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression, level or activity of genes other than MCH or MCH-R (e.g., other genes associated with an insulin disorder, or other genes on an array). The data record can be structured as a table, e.g., a table that is part of a database such as a relational database (e.g., a SQL database of the Oracle or Sybase database environments). The invention also includes a method of communicating information about a subject, e.g., by transmitting information, e.g., transmitting a computer readable record described herein, e.g., over a computer network.

In another aspect, the invention features a method of providing information, e.g., for making a decision with regard to the treatment of a subject having, or at risk for, an insulin disorder described herein. The method includes (a) evaluating the expression, level or activity of MCH or MCH-R; optionally (b) providing a value for the expression, level or activity of MCH or MCH-R; optionally (c) comparing the provided value with a reference value, e.g., a control or non-disease state reference or a disease state reference; and optionally (d) based, e.g., on the relationship of the provided value to the reference value, supplying information, e.g., information for making a decision on or related to the treatment of the subject.

In a preferred embodiment, the provided value relates to an activity described herein, e.g., to a binding activity of MCH or MCH-R.

In a preferred embodiment, the decision is whether to administer a preselected treatment.

In a preferred embodiment, the decision is whether a party, e.g., an insurance company, HMO, or other entity, will pay for all or part of a preselected treatment.

Also featured is a method of evaluating a sample. The method includes providing a sample, e.g., from the subject, and determining a gene expression profile of the sample, wherein the profile includes a value representing the level of expression of a MCH or MCH-R. The method can further include comparing the value or the profile (i.e., multiple values) to a reference value or reference profile. The gene expression profile of the sample can be obtained by methods known in the art (e.g., by providing a nucleic acid from the sample and contacting the nucleic acid to an array). The method can be used to diagnose an insulin related disorder, e.g., an insulin related disorder described herein, in a subject wherein misexpression of an MCH signaling molecule, e.g., MCH or MCH-R, is an indication that the subject has or is disposed to having an insulin related disorder, e.g., an insulin related disorder described herein. The method can be used to monitor a treatment for an insulin related disorder in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) Science 286:531).

In another aspect, the invention features a method of evaluating a gene for its involvement in an insulin related disorder, e.g., in an insulin related disorder described herein. The method includes (a) providing a cell, tissue, or animal in which MCH signaling is perturbed, e.g., MCH or MCH-R is perturbed, (b) evaluating the expression of one or more genes in the cell, tissue, or animal, and (c) optionally comparing the expression of the one or more genes in the cell, tissue, or animal with a reference, e.g., with the expression of the one or more genes in a control cell, tissue or animal. A gene or genes identified as increased or decreased in the cell, tissue, or animal as compared to the reference, e.g., the control, are identified as candidate genes involved in an insulin related disorder, e.g., an insulin related disorder described herein.

In a preferred embodiment, the cell or tissue is from a subject (e.g., a human or non-human animal, e.g., an experimental animal) having or being at risk for an insulin disorder, e.g., an insulin disorder described herein.

In a preferred embodiment, the animal is a transgenic animal, e.g., a transgenic animal having a knock-out or overexpressing mutation for a component of the MCH signaling pathway, e.g., MCH or MCH-R.

In yet another aspect, the invention features a method of evaluating a test compound, e.g., evaluating a test compound for the ability to modulate MCH signaling. The method includes providing or obtaining a cell or tissue that naturally expresses MCH and MCHR, e.g., an islet cell or tissue, e.g., an islet cell or tissue (e.g., a RINm5F or bTC3 cell line); providing or obtaining a test compound; and evaluating the ability of the test compound to modulate MCH signaling in the islet cell or tissue. The method can be performed using routine screening techniques. In preferred embodiments, the islet cell or tissue is not transfected with an MCH or MCHR transgene.

In yet another aspect, the invention features a method of evaluating a test compound. The method includes providing a cell and a test compound; contacting the test compound to the cell; obtaining a subject expression profile for the contacted cell; and comparing the subject expression profile to one or more reference profiles. The profiles include a value representing the level of expression of a component of the MCH signaling pathway, e.g., MCH or MCH-R. In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

In another aspect, the invention features, a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of expression of a component of the MCH signaling pathway, e.g., MCH or MCH-R. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile; access a database of reference expression profiles; and either i) select a matching reference profile most similar to the subject expression profile or ii) determine at least one comparison score for the similarity of the subject expression profile to at least one reference profile. The subject expression profile, and the reference expression profiles each include a value representing the level of expression of a component of the MCH signaling pathway, e.g., MCH or MCH-R.

As used herein, "treatment" or "treating a subject" is defined as the application or administration of a therapeutic agent to a patient, or application or administration of a therapeutic agent to an isolated tissue or cell line from a patient, e.g., a pancreatic tissue, e.g., an islet tissue, or β-cell, who has a disease, a symptom of disease or a predisposition toward a disease, e.g., an insulin related disorder, e.g., an insulin disorder described herein. Treatment can slow, cure, heal, alleviate, relieve, alter, remedy, ameliorate, improve or affect the disease, a symptom of the disease or the predisposition toward disease, e.g., by at least 10%.

As used herein, to ability of a first molecule to "interact" with a second molecule refers to the ability of the first molecule to act upon the structure and/or activity of the second molecule, either directly or indirectly. For example, a first molecule can interact with a second by (a) directly binding, e.g., specifically binding, the second molecule, e.g., transiently or stably binding the second molecule; (b) modifying the second molecule, e.g., by cleaving a bond, e.g., a covalent bond, in the second molecule, or adding or removing a chemical group to or from the second molecule, e.g., adding or removing a phosphate group or carbohydrate group; (c) modulating an enzyme that modifies the second molecule, e.g., inhibiting or activating a kinase or phosphatase that normally modifies the second molecule; (d) affecting expression of the second molecule, e.g., by binding, activating, or inhibiting a control region of a gene encoding the second molecule, or binding, activating, or inhibiting a transcription factor that associates with the gene encoding the second molecule; (d) affecting the stability of an mRNA encoding the second molecule, e.g., by inhibiting mRNAse activity against the mRNA encoding the second molecule or by degrading the mRNA encoding the second molecule.

DETAILED DESCRIPTION

The inventors have found that overexpression of MCH results in increased plasma insulin concentration and increased pancreatic islet size. The data described herein indicate that MCH stimulates insulin release from the islets/β-cells via its own receptor. The inventors have thus found that components of the MCH signaling pathway, e.g., MCH or MCH-R (e.g., MCH-R1 or MCH-R2) are targets for the diagnosis and treatment of insulin related disorders, e.g., insulin related disorders described herein.

Analogs Of MCH

The sequence of the cyclic MCH peptide is as follows. NH2-Asp-Phe-Asp-Met-Leu-Arg-Cys-Met-Leu-Gly-Arg-Val-Tyr-Arg-Pro-Cys-Trp-Gln-Val-COOH (SEQ ID NO:1). The importance of the disulfide bond for activity has been demonstrated by chemical reduction and by the synthesis of ring contraction analogs, both of which eliminated ligand activity. Chemical modification of either the Tyr or Arg residues significantly reduces activity. Truncation at either the carboxy or amino terminus results in no loss of activity, with the minimum peptide analog retaining the potency of the native peptide being MCH(5-15). Arg11 has been identified as a requisite residue for binding of human MCH to its receptor, confirming the importance of the cyclic core of MCH as the major pharmacophore of MCH receptor function (Macdonald et al. (2000) Mol Pharmacol 58(1):217-25).

Synthetic MCH and its analogs can be prepared using art-recognized methods to identify agonists and antagonists, and determine the structural requirements for MCH agonist or antagonist activity. MCH can be modified in a number of ways, e.g., by shortening either (or both) the amino- or carboxy-terminal regions, contracting the cysteine bridged ring, forming acyclic analogs, or modifying or substituting an amino acid, e.g., a residue, within, or outside, the ring. Synthetic MCH and its analogs can be assayed using one or more of the assays described herein.

Generally, the synthetic schemes use the Merrifield solid phase synthesis followed by cyclization and purification as described, e.g., in Lebl et al. (1988) J. Med. Chem. 31:949-954, herein incorporated by reference. Briefly, chloromethylated resin can be used as the support to introduce the first amino acid on an automated synthesizer, e.g. a DuPont 2200. The intact peptides are cleaved from the resin and then washed. Following extraction from the wash the peptides are lyophilized. The lyophilized protein is dissolved in degassed water. Cyclization is achieved by the dropwise addition of potassium ferricyanide ($K_3Fe(CN)_6$). Purification can be performed by column chromatography on Sephadex G-25, carboxymethyl cellulose and by reversed-phase high-performance chromatography (HPLC).

Alternatively, truncated MCH analogs can be prepared by exposing natural or synthetic MCH to enzymes. Natural MCH can be isolated from pituitaries using an acetone extraction and purified on an HPLC column as described in Kawauchi et al. (1988) Adv. in Pigment Cell Res. 517-530, herein incorporated by reference. For example, MCH.sub.1-14, a carboxy-terminal truncation, can be generated from MCH by exposure to carboxypeptidase Y.

Acyclic analogs can be constructed by replacing the Cys.sup.5-Cys.sup.14 bridge with pseudoisosteric residues. Either L-serine, a polar substitute, or L-.alpha.-aminobutyrate, a non-polar substitute, can be utilized. The peptides, with the appropriate substitution, can be prepared by solid phase synthesis as described above and in Matsunaga et al., Life Sci. (1992) 51:679-685, herein incorporated by reference.

Modification of amino acids within the ring is performed with a reagent specific to each residue. Modifications can be accomplished either by substituting a different amino acid or altering the existing amino acid. For example, Arg (11) is a critical residue for MCH function (Macdonald et al. (2000) Mol Pharmacol 58(1):217-25). The Tyr residue at position 11 can be modified with the addition of a $-NO_2$ group by exposing MCH to a solution of 10% nitromethane-95% ethanol. See, e.g., Kawauchi et al. (1988) Adv. in Pigment Cell Res. 517-530, herein incorporated by reference.

Structural Requirements for MCH Activity

A significant amount of work has been done on determining structural requirements for MCH. The ring structure of MCH has been found in a number of studies to be important for activity.

Numerous investigators have synthesized N-terminal and C-terminal fragment analogs of salmon MCH and have tested them for MCH activity in teleost skin bioassay and frog and lizard bioassays, described herein (see, e.g., Matsunaga et al. (1989) *Peptides* 10:349-354; Hardley et al. (1987) *Life Sci.* 40:1139-1145, herein incorporated by reference). These studies have concluded that the minimal sequence needed to elicit an equipotent response to the native MCH is MCH(5-15), a structure which lacks residues 1-4 from the N-terminal end, and residues 16-17 of the C-terminal end of the peptide. The removal of $Trp^{15}$, producing a fragment MCH(5-14), results in an analog 100 to 300 less active than native MCH indicating that Trp at position 15 is important for maintenance of full (equipotent) agonist activity of MCH, and that indole ring of Trp residue may be important in aiding the fit of MCH into its receptor pocket, thus facilitating binding. Because fragment analogs, which are N terminal deleted, e.g., those lacking residues 1-4, are equipotent to native MCH, they appear to not be required for MCH activity. The same was concluded for residues 16-17 in the C-terminal end of the peptide.

Furthermore, other investigators have synthesized MCH analogs with contracted ring structure and have tested them for activity in teleost fish skin bioassay (see, e.g., Lebl et al. (1988) *J. Med. Chem.* 31:949-954; Lebl et al. (1989) *Life Sci.* 44:451-457; Matsunaga et al. (1989) *Peptides* 10:349-354, herein incorporated by reference). The following ring contraction analogs (which retain a disulfide bond) were synthesized: [Ala$^5$, Cys$^{10}$]MCH, [Ala$^5$, Cys$^8$]MCH, [Ala$^5$, Cys$^7$]MCH, [Ala$^5$, Cys$^{10}$]MCH$_{5-17}$, [Ala$^5$, Cys$^8$]MCH$_{5-17}$, [Ala$^5$, Cys$^7$]MCH$_{5-17}$, [Cys$^{10}$]MCH$_{10-17}$, [Cys$^8$]MCH$_{8-17}$, and [Cys$^7$]MCH$_{7-17}$. The studies with these analogs have concluded that the disulfide bond between positions 5 and 14 is essential for the MCH-like activity, because ring contractions eliminated or greatly reduced the MCH-like activity. It seems that the 10 ring residue structure, MCH(5-14) is very important for optimal activation. Surprisingly, two of the analogs, [Ala$^5$, Cys$^8$]MCH$_{5-17}$ and [Cys$^{10}$]MCH$_{10-17}$, were found to be full agonists, however, with very reduced potency, indicating that the shortest sequence having MCH-like activity may be comprised of residues 10-14 (Val-Tyr-Arg-Pro-Cys; residues 12-16 of SEQ ID NO:1) with residues at positions 11-14 (Tyr-Arg-Pro-Cys; residues 13-16 of SEQ ID NO:1) possibly being crucial for message transduction.

In addition, acyclic analogs have been synthesized and tested for MCH activity in teleost fish skin bioassay (see, e.g., Kawauchi and Kawazoe (1988) *Advances in Pigment Cell Res.* 517-527; Matsunaga et al. (1992) *Life Sci.* 51:679-685, herein incorporated by reference). These analogs were constructed so that they differed form native MCH only in the polarity of the side chain group at positions 5 and 14. For one analog polar L-serine was substituted for cysteine at positions 5 and 14 (L-Ser$^{5,14}$ MCH), while for the other analog, non-polar L α-aminobutyrate (Abu) was substituted at the same positions (Abu$^{5,14}$ MCH). Another acyclic analog was constructed by reduction of the disulfide bond, followed by subsequent carboxymethylation of Cys residues at positions 5 and 14 (CAM-Cys$^{5,14}$ MCH). All of these analogs exhibited no MCH-like activity, suggesting that the disulfide bridge is necessary to maintain correct conformation and topographical features of MCH for receptor binding and transmembrane signal transduction.

MCH derivatives with modified residues have also been synthesized and tested for activity in fish scale assay (see, e.g., Kawauchi and Kawazoe (1988) *Advances in Pigment Cell Res.* 517-527, herein incorporated by reference). The following derivatives have been synthesized and tested for activity: NPS-Trp$^{15}$MCH, DHCH-Arg$^{4,9,12}$MCH, NO$_2$-Tyr$^{11}$MCH and S-O-Met$^{3,6}$MCH. Modifications of amino acid residues outside of the ring structure had no effect on the MCH activity, while the modifications of residues within the ring, e.g., DHCH-Arg$^{4,9,12}$MCH, NO$_2$-Tyr$^{11}$MCH and S-O-Met$^{3,6}$MCH, resulted in analogs with greatly reduced MCH activity. These results support the suggestion that the MCH activity is elicited from the cyclic segment (MCH5-14) of the peptide. Indeed, a compound consisting merely of the cyclic core of human MCH with the Arg attached to the N-terminus of the disulfide ring (Arg-cyclo(S-S)(Cys-Met-Leu-Gly-Arg-Val-Tyr-Arg-Pro-Cys) (SEQ ID NO:2) can activate both human MCH-1R and human MCH-2R receptors about as effectively as full-length human MCH (Bednarek et al. (2001) Biochemistry 40(31):9379-86). Selective antagonists, e.g., for hMCH-1R, are also known in the art (see, e.g., Bednarek et al. (2002) Biochemistry 41(20):6383-90; and Borowsky et al. (2002) Nat Med 8(8): 825-30).

Audinot et al. (J Biol Chem. (2001) 276(17):13554-62) made numerous alanine scanning peptide analogs of MCH and tested the mutant peptides for activity against a human cell transfected with a human MCH receptor. Using this assay system, Audinot et al. found numerous antagonists (8 of 57 mutant peptides made). All of the antagonists included changes in the MCH ring structure.

Non-peptide antagonists or agonists of MCH are also known and can be readily identified. For example, Takekawa et al. (2002) European J. Pharmacol. 438:129-135 used a combination of in vitro and in vivo testing to identify the MCH antagonist T-226296, a (−) enantiomer of N-[6-(dimethylamino)-methyl]-5,6,7,8-tetrahydro-2-naphthalenyl]-4'-fluoro[1,1'-biphenyl]-4-carboxamide, from a library of chemical compounds.

Analogs of MCH Receptor

Human MCH receptors and analogs and variants thereof are described in: Chambers et al. (1999) Nature 400(6741): 261-5 and Saito et al. (1999) Nature 400(6741):265-9 (MCH-R1); Rodriguez et al. (2001) Mol Pharmacol. 60(4): 632-9, Wang et al. (2001) J Biol Chem. 276(37):34664-70, Sailer et al. (2001) Proc Natl Acad Sci U S A 98(13):7564-9 and Hill et al (2001) J. Biol. Chem. 276 (23),:20125-20129 (MCH-R2); Mori et a (2001) Biochem Biophys Res Commun. 283(5):1013-8 (SLT); and U.S. Pat. Nos. 6,291,195; 6,221,616; and 6,221,613, all of which are incorporated herein by reference. The amino acid and nucleotide (coding) sequence of the human MCH-R1 (also known as SLC-1) and MCH-R2 receptors can be found online (GenBank Accession No. AB063174 and AF347063, respectively). For a review of MCH receptors, see Boutin et al. (2002) Can J Physiol Pharmacol 80(5):388-95.

Critical residues involved in binding and activation of the MCH/receptor complex are identified in Macdonald et al. (2000) Mol Pharmacol 58(1):217-25. E.g., Macdonald et al. conclude that Asp(123)(3.32) in the MCH receptor is required for the formation of the MCH peptide/receptor complex and form a direct interaction that is critical for receptor function.

Assays for MCH Signaling Activity

The activity of compounds, e.g., MCH analogs, e.g., MCH agonists or antagonists, and MCH receptor analogs, e.g., MCH receptor agonists or antagonists, can be determined by a number of in vitro, ex-vivo and in vivo assays for MCH signaling activity known in the art. Examples of such assays can be found, e.g., in U.S. Pat. No. 5,849,708; Audinot et al. (2001) J Biol Chem. 276(17):13554-62; and Macdonald et al. (2000) Mol Pharmacol 58(1):217-25, all of which are incorporated herein by reference. Furthermore, the activity of an analog, e.g., an MCH or MCH receptor agonist or antagonist described herein, can be determined in the methods described herein by evaluating the ability of the subject analog to stimulate insulin release from pancreas, isolated islets or islet equivalents, isolated β-cells, or in vivo in an animal, e.g., a rodent. Insulin secretion, e.g., from an islet or β-cell, can be measured by, e.g., standard detection techniques, including enzyme linked immunosorbent assays (ELISAs), immunoprecipitations, immunofluorescence, enzyme immunoassay (EIA), radioimmunoassay (RIA), and Western blot analysis.

Generation of Variants: Production of Altered DNA and Peptide Sequences by Random Methods Amino acid sequence variants of components of the MCH signaling pathway, e.g., MCH or MCH-R, or fragments thereof, can be prepared by random mutagenesis of DNA which encodes a component of the MCH signaling pathway, e.g., MCH or MCH-R or a region thereof. Useful methods include PCR mutagenesis and saturation mutagenesis, as described below. A library of random amino acid sequence variants can also be generated by the synthesis of a set of degenerate oligonucleotide sequences.

PCR Mutagenesis

In PCR mutagenesis, reduced Taq polymerase fidelity is used to introduce random mutations into a cloned fragment of DNA (Leung et al., 1989, *Technique* 1:11-15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Olizonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, SA (1983) *Tetrahedron* 39:3; Itakura et al. (1981) *Recombinant DNA, Proc 3rd Cleveland Sympos. Macromolecules*, ed. A G Walton, Amsterdam: Elsevier pp273-289; Itakura et al. (1984) *Annu. Rev. Biochem*. 53:323; Itakura et al. (1984) *Science* 198:1056; Ike et al. (1983) *Nucleic Acid Res*. 11:477. Such techniques have been employed in the directed evolution of other proteins (see, for example, Scott et al. (1990) *Science* 249:386-390; Roberts et al. (1992) *PNAS* 89:2429-2433; Devlin et al. (1990) *Science* 249: 404-406; Cwirla et al. (1990) PNAS 87: 6378-6382; as well as U.S. Pat. Nos. 5,223,409, 5,198,346, and 5,096,815).

Generation of Variants: Production of Altered DNA and Peptide Sequences by Directed Mutagenesis Non-random or directed, mutagenesis techniques can be used to provide specific sequences or mutations in specific regions. These techniques can be used to create variants which include, e.g., deletions, insertions, or substitutions, of residues of the known amino acid sequence of a protein. The sites for. mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1-3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081-1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. NatL. Acad. Sci.* (1978) USA, 75: 5765).

Cassette Mutagenesis

Another method for preparing variants, cassette mutagenesis, is based on the technique described by Wells et al. (*Gene*, 1985, 34:315). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate mutants. For example, the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screening Libraries of Peptide Fragments or Homologs Various techniques are known in the art for screening peptides, e.g., synthetic peptides, antibodies or antigen binding fragments thereof, small molecular weight peptides (e.g., linear or cyclic peptides) or generated mutant gene products. Techniques for screening large gene libraries often include cloning the gene library into replicable expression vectors, transforming appropriate cells with the resulting library of vectors, and expressing the genes under conditions in which detection of a desired activity, e.g., binding to a natural ligand, e.g., a receptor or substrate, facilitates relatively easy isolation of the vector encoding the gene whose product was detected. Each of the techniques described below is amenable to high through-put analysis for screening large numbers of sequences created, e.g., by random mutagenesis techniques.

Two Hybrid Systems

Two hybrid (interaction trap) assays can be used to identify a protein that interacts with a component of the MCH signaling pathway, e.g., MCH or MCH-R or active fragments thereof. These may include, e.g., agonists, superagonists, and antagonists of MCH signaling. (The subject protein and a protein it interacts with are used as the bait protein and fish proteins.). These assays rely on detecting the reconstitution of a functional transcriptional activator mediated by protein-protein interactions with a bait protein. In particular, these assays make use of chimeric genes which express hybrid proteins. The first hybrid comprises a DNA-binding domain fused to the bait protein, e.g., a component of the MCH signaling pathway, e.g., MCH or MCH-R or active fragments thereof. The second hybrid protein contains a transcriptional activation domain fused to a "fish" protein, e.g. an expression library. If the fish and bait proteins are able to interact, they bring into close proximity the DNA-binding and transcriptional activator domains. This proximity is sufficient to cause transcription of a reporter gene which is operably linked to a transcriptional regulatory site which is recognized by the DNA binding domain, and expression of the marker gene can be detected and used to score for the interaction of the bait protein with another protein.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) Bio/Technology 9:1370-1371; and Goward et al. (1992) TIBS 18:136-140). This technique was used in Sahu et al. (1996) J. Immunology 157:884-891, to isolate an inhibitor of a target protein. In a similar fashion, a detectably labeled ligand can be used to score for potentially functional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical E. coli filamentous phages M13, fd., and fl are most often used in phage display libraries. Either of the phage gIII or gVIII coat proteins can be used to generate fusion proteins without disrupting the ultimate packaging of the viral particle. Foreign epitopes can be expressed at the NH2-terminal end of pIII and phage bearing such epitopes recovered from a large excess of phage lacking this epitope (Ladner et al. PCT publication WO 90/02909; Garrard et al., PCT publication WO 92/09690; Marks et al. (1992) J. Biol. Chem. 267: 16007-16010; Griffiths et al. (1993) EMBO J 12:725-734; Clackson et al. (1991) Nature 352:624-628; and Barbas et al. (1992) PNAS 89:4457-4461).

A common approach uses the maltose receptor of E. coli (the outer membrane protein, LamB) as a peptide fusion partner (Charbit et al. (1986) EMBO 5, 3029-3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) Vaccines 91, pp. 387-392), PhoE (Agterberg, et al. (1990) Gene 88, 37-45), and PAL (Fuchs et al. (1991) Bio/Tech 9, 1369-1372), as well as large bacterial surface structures have served as vehicles for peptide display. Peptides can be fused to pilin, a protein which polymerizes to form the pilus-a conduit for interbacterial exchange of genetic information (Thiry et al. (1989) Appl. Environ. Microbiol. 55, 984-993). Because of its role in interacting with other cells, the pilus provides a useful support for the presentation of peptides to the extracellular environment.

Another large surface structure used for peptide display is the bacterial motive organ, the flagellum. Fusion of peptides to the subunit protein flagellin offers a dense array of may peptides copies on the host cells (Kuwajima et al. (1988) *Bio/Tech*. 6, 1080-1083). Surface proteins of other bacterial species have also served as peptide fusion partners. Examples include the *Staphylococcus* protein A and the outer membrane protease IgA of *Neisseria* (Hansson et al. (1992) *J. Bacteriol*. 174, 4239-4245 and Klauser et al. (1990) *EMBO J*. 9, 1991-1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) *PNAS USA* 89:1865-1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) *Proc. Natl. Acad. Sci. U.S.A.* 89-1869)

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) *Proc. Natl. Acad. Sci. U.S.A.* 87, 6378-6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al. (1994) *J. Med. Chem*. 37(9):1233-1251). These particular biases are not a factor in the LacI display system.

The number of small peptides available in recombinant random libraries is enormous. Libraries of $10^7$-$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3-6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem*. 37(9):1233-1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem* 204,357-364). To identify the sequences of the active peptides one sequences the DNA produced by the phagemid host.

Secondary Screens for Modulators of MCH Signaling

The high through-put assays described above can be followed (or substituted) by secondary screens in order to identify biological activities which will, e.g., allow one skilled in the art to differentiate agonists from antagonists. The type of a screen used will depend on the desired activity that needs to be tested. For example, an assay can be developed in which the ability of a candidate agent to modulate insulin secretion (e.g., from a β cell, islet tissue or pancreatic tissue) can be used to identify antagonists or agonists from a group of peptide fragments isolated though one of the primary screens described above.

Peptide Mimetics

The invention also provides for production of the protein binding domains of components of the MCH signaling pathway, e.g., MCH or MCH-R, to generate mimetics, e.g. peptide or non-peptide agents, e.g., inhibitory agents. See, for example, "Peptide inhibitors of human papillomavirus protein binding to retinoblastoma gene protein" European patent applications EP 0412 762and EP 0031 080.

Non-hydrolyzable peptide analogs of critical residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffinan et al. in Peptides: Chemistry and Biology, G.R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill. 1985), b-turn dipeptide cores (Nagai et al. (1985) Tetrahedron Lett 26:647; and Sato et al. (1986) J Chem Soc Perkin Trans 1:1231), and b-aminoalcohols (Gordon et al. (1985) Biochem Biophys Res Communl26:419; and Dann et al. (1986) Biochem Biophys Res Commun 134:71).

Antibodies

An agent described herein, e.g., a modulator of a component of the MCH signaling pathway, e.g., MCH or MCH-R, can also be an antibody specifically reactive with a component of the MCH signaling pathway, e.g., MCH or MCH-R. An antibody can be an antibody or a fragment thereof, e.g., an antigen binding portion thereof. As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

The term "antigen-binding fragment" of an antibody (or simply "antibody portion," or "fragment"), as used herein, refers to one or more fragments of a full-length antibody that retain the ability to specifically bind to an antigen (e.g., a polypeptide encoded by a nucleic acid of Group I or II). Examples of binding fragments encompassed within the term "antigen-binding fragment" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate nucleic acids, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. The term "monoclonal antibody" or "monoclonal antibody composition", as used herein, refers to a population of antibody molecules that contain only one species of an antigen binding site capable of immunoreacting with a particular epitope. A monoclonal antibody composition thus typically displays a single binding affinity for a particular protein with which it immunoreacts.

Anti-protein/anti-peptide antisera or monoclonal antibodies can be made as described herein by using standard protocols (See, for example, Antibodies: A Laboratory Manual ed. by Harlow and Lane (Cold Spring Harbor Press: 1988)).

A component of the MCH signaling pathway, e.g., MCH or MCH-R, can be used as an immunogen to generate antibodies that bind the component using standard techniques for polyclonal and monoclonal antibody preparation. The full-length component protein can be used or, alternatively, antigenic peptide fragments of the component can be used as immunogens.

Typically, a peptide is used to prepare antibodies by immunizing a suitable subject, (e.g., rabbit, goat, mouse or other mammal) with the immunogen. An appropriate immunogenic preparation can contain, for example, a recombinant MCH or MCH-R peptide, or a chemically synthesized MCH or MCH-R peptide or antagonist. See, e.g., U.S. Pat. No. 5,460,959; and co-pending U.S. applications Ser No. 08/334,797; U.S. Ser No. 08/231,439; U.S. Ser No. 08/334, 455; and U.S. Ser No. 08/928,881, which are hereby expressly incorporated by, reference in their entirety. The nucleotide and amino acid sequences of MCH and MCH-R described herein are known. The preparation can further include an adjuvant, such as Freund's complete or incomplete adjuvant, or similar immunostimulatory agent. Immunization of a suitable subject with an immunogenic component of the MCH signaling pathway, e.g., MCH or MCH-R, or fragment preparation induces a polyclonal antibody response.

Additionally, antibodies produced by genetic engineering methods, such as chimeric and humanized monoclonal antibodies, comprising both human and non-human portions, which can be made using standard recombinant DNA techniques, can be used. Such chimeric and humanized monoclonal antibodies can be produced by genetic engineering using standard DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al., Science 240:1041-1043, 1988; Liu et al., PNAS 84:3439-3443, 1987; Liu et al., J. Immunol. 139:3521-3526, 1987; Sun et al. PNAS 84:214-218, 1987; Nishimura et al., Canc. Res. 47:999-1005, 1987; Wood et al., Nature 314:446-449, 1985; and Shaw et al., J. Natl. Cancer Inst. 80:1553-1559, 1988); Morrison, S. L., Science 229: 1202-1207, 1985; Oi et al., BioTechniques 4:214, 1986; Winter U.S. Pat. No. 5,225,539; Jones et al., Nature 321: 552-525, 1986; Verhoeyan et al., Science 239:1534, 1988; and Beidler et al., J. Immunol. 141:4053-4060, 1988.

In addition, a human monoclonal antibody directed against a component of the MCH signaling pathway, e.g., MCH or MCH-R, can be made using standard techniques. For example, human monoclonal antibodies can be generated in transgenic mice or in immune deficient mice engrafted with antibody-producing human cells. Methods of generating such mice are describe, for example, in Wood et al. PCT publication WO 91/00906, Kucherlapati et al. PCT publication WO 91/10741; Lonberg et al. PCT publication WO 92/03918; Kay et al. PCT publication WO 92/03917; Kay et al. PCT publication WO 93/12227; Kay et al. PCT publication 94/25585; Rajewsky et al. Pct publication WO 94/04667; Ditullio et al. PCT publication WO 95/17085; Lonberg, N. et al. (1994) Nature 368:856-859; Green, L. L. et al. (1994) Nature Genet. 7:13-21; Morrison, S. L. et al. (1994) Proc. Natl. Acad. Sci. USA 81:6851-6855; Bruggeman et al. (1993) Year Immunol 7:33-40; Choi et al. (1993) Nature Genet. 4:117-123; Tuaillon et al. (1993) PNAS 90:3720-3724; Bruggeman et al. (1991) Eur J Immunol 21:1323-1326); Duchosal et al. PCT publication WO 93/05796; U.S. Pat. No. 5,411,749; McCune et al. (1988) Science 241:1632-1639), Kamel-Reid et al. (1988) Science 242:1706; Spanopoulou (1994) Genes & Development 8:1030-1042; Shinkai et al. (1992) Cell 68:855-868). A human antibody-transgenic mouse or an immune deficient mouse engrafted with human antibody-producing cells or tissue can be immunized with a component of the MCH signaling pathway, e.g., MCH or MCH-R, or an antigenic peptide thereof, and splenocytes from these immunized mice can then be used to create hybridomas. Methods of hybridoma production are well known.

Human monoclonal antibodies against a component of the MCH signaling pathway, e.g., MCH or MCH-R, can also be prepared by constructing a combinatorial immunoglobulin library, such as a Fab phage display library or a scFv phage display library, using immunoglobulin light chain and heavy chain cDNAs prepared from mRNA derived from lymphocytes of a subject. See, e.g., McCafferty et al. PCT publication WO 92/01047; Marks et al. (1991) J. Mol. Biol. 222:581-597; and Griffths et al. (1993) EMBO J 12:725-734. In addition, a combinatorial library of antibody variable regions can be generated by mutating a known human antibody. For example, a variable region of a human antibody known to bind a component of the MCH signaling pathway, e.g., MCH or MCH-R, can be mutated, by for example using randomly altered mutagenized oligonucleotides, to generate a library of mutated variable regions which can then be screened to bind to a component of the MCH signaling pathway, e.g., MCH or MCH-R. Methods of inducing random mutagenesis within the CDR regions of immunoglobin heavy and/or light chains, methods of crossing randomized heavy and light chains to form pairings and screening methods can be found in, for example, Barbas et al. PCT publication WO 96/07754; Barbas et al. (1992) Proc. Nat'l Acad. Sci. USA 89:4457-4461.

The immunoglobulin library can be expressed by a population of display packages, preferably derived from filamentous phage, to form an antibody display library. Examples of methods and reagents particularly amenable for use in generating antibody display library can be found in, for example, Ladner et al. U.S. Pat. No. 5,223,409; Kang et al. PCT publication WO 92/18619; Dower et al. PCT publication WO 91/17271; Winter et al. PCT publication WO 92/20791; Markland et al. PCT publication WO 92/15679; Breitling et al. PCT publication WO 93/01288; McCafferty et al. PCT publication WO 92/01047; Garrard et al. PCT publication WO 92/09690; Ladner et al. PCT publication WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffths et al. (1993) supra; Hawkins et al. (1992) J Mol Biol 226:889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982. Once displayed on the surface of a display package (e.g., filamentous phage), the antibody library is screened to identify and isolate packages that express an antibody that binds a component of the MCH signaling pathway, e.g., MCH or MCH-R. In a preferred embodiment, the primary screening of the library involves panning with an immobilized component of the MCH signaling pathway, e.g., MCH or MCH-R, and display packages expressing antibodies that bind immobilized proteins described herein are selected.

Antisense Nucleic Acid Sequences

Nucleic acid molecules which are antisense to a nucleotide encoding a component of the MCH signaling pathway, e.g., MCH or MCH-R, can also be used as an agent which inhibits expression of MCH signaling. An "antisense" nucleic acid includes a nucleotide sequence which is complementary to a "sense" nucleic acid encoding the component, e.g., complementary to the coding strand of a double-stranded cDNA molecule or complementary to an mRNA sequence. Accordingly, an antisense nucleic acid can form hydrogen bonds with a sense nucleic acid. The antisense nucleic acid can be complementary to an entire coding strand, or to only a portion thereof. For example, an antisense nucleic acid molecule which antisense to the "coding region" of the coding strand of a nucleotide sequence encoding the component can be used.

The coding strand sequences encoding MCH and MCH-R are known. Given the coding strand sequences encoding these proteins, antisense nucleic acids can be designed according to the rules of Watson and Crick base pairing. The antisense nucleic acid molecule can be complementary to the entire coding region of mRNA, but more preferably is an oligonucleotide which is antisense to only a portion of the coding or noncoding region of mRNA. For example, the antisense oligonucleotide can be complementary to the region surrounding the translation start site of the mRNA. An antisense oligonucleotide can be, for example, about 5, 10, 15, 20, 25, 30, 35, 40, 45 or 50 nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5- oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest.

Administration

An agent that modulates a component of the MCH signaling pathway, e.g., MCH or MCH-R, e.g., an agent described herein, can be administered to a subject by standard methods. For example, the agent can be administered by any of a number of different routes including intravenous, intradermal, subcutaneous, oral (e.g., inhalation), transdermal (topical), and transmucosal, or direct administration, e.g., onto the surface of the eye. In one embodiment, the modulating agent can be administered orally. In another embodiment, the agent is administered by injection, e.g., intramuscularly, or intravenously. In a preferred embodiment, the agent is administered directly onto the surface of the eye.

The agent that modulates a component of the MCH signaling pathway, e.g., MCH or MCH-R, e.g., an agent described herein, e.g., nucleic acid molecules, polypeptides, fragments or analogs, modulators, organic compounds and antibodies (also referred to herein as "active compounds") can be incorporated into pharmaceutical compositions suitable for administration to a subject, e.g., a human. Such compositions typically include the nucleic acid molecule, polypeptide, modulator, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions of the invention. Supplementary active compounds can also be incorporated into the compositions.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an agent described herein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

The nucleic acid molecules described herein can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al., PNAS 91:3054-3057, 1994). The pharmaceutical preparation of the gene therapy vector can include the gene therapy vector in an acceptable diluent, or can include a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

Gene Therapy

The nucleic acids described herein, e.g., an antisense nucleic acid described herein, can be incorporated into gene constructs to be used as a part of a gene therapy protocol to deliver nucleic acids encoding either an agonistic or antagonistic form of a molecule described herein. The invention features expression vectors for in vivo transfection and expression of an MCH signaling molecule described herein in particular cell types so as to reconstitute the function of, or alternatively, antagonize the function of the component in a cell in which that polypeptide is misexpressed. Expression constructs of such components may be administered in any biologically effective carrier, e.g. any formulation or composition capable of effectively delivering the component gene to cells in vivo. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or CaPO4 precipitation carried out in vivo.

A preferred approach for in vivo introduction of nucleic acid into a cell is by use of a viral vector containing nucleic acid, e.g. a cDNA, encoding a component of the MCH signaling pathway, e.g., MCH or MCH-R. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These. vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) Blood 76:271). A replication defective retrovirus can be packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include *Crip, *Cre, *2 and *Am. Retroviruses have been used to introduce a variety of genes into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) J. Virol. 57:267).

Yet another viral vector system useful for delivery of the subject gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. (1992) Curr. Topics in Micro. and Immunol.158:97-129). It is also one of the few viruses that may integrate its DNA into non-dividing cells, and exhibits a high frequency of stable integration (see for example Flotte et al. (1992) Am. J. Respir. Cell. Mol. Biol. 7:349-356; Samulski et al. (1989) J. Virol. 63:3822-3828; and McLaughlin et al. (1989) J. Virol. 62:1963-1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251-3260 can be used to introduce DNA into cells. A variety of nucleic acids have been introduced into different cell types using AAV vectors (see for example Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J. Virol. 51:611-619; and Flotte et al. (1993) J. Biol. Chem. 268:3781-3790).

In addition to viral transfer methods, such as those illustrated above, non-viral methods can also be employed to cause expression of a component of the MCH signaling pathway, e.g., MCH or MCH-R, in the tissue of a subject. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject gene by the targeted cell. Exemplary gene delivery systems of this type include liposomal derived systems, poly-lysine conjugates, and artificial viral envelopes. Other embodiments include plasmid injection systems such as are described in Meuli et al. (2001) J Invest Dermatol. 116(1): 131-135; Cohen et al. (2000) Gene Ther 7(22):1896-905; or Tam et al. (2000) Gene Ther 7(21):1867-74.

In a representative embodiment, a gene encoding a component of the MCH signaling pathway, e.g., MCH or MCH-R, can be entrapped in liposomes bearing positive charges on their surface (e.g., lipofectins) and (optionally) which are tagged with antibodies against cell surface antigens of the target tissue (Mizuno et al. (1992) No Shinkei Geka 20:547-551; PCT publication WO 91/06309; Japanese patent application 1047381; and European patent publication EP-A-43075).

In clinical settings, the gene delivery systems for the therapeutic gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054-3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system.

Cell Therapy

A component of the MCH signaling pathway, e.g., MCH or MCH-R, can also be increased in a subject by introducing into a cell, e.g., an endothelial cell, a nucleotide sequence that modulates the production of a component of the MCH signaling pathway, e.g., MCH or MCH-R, e.g., a nucleotide sequence encoding MCH or MCH-R polypeptide or functional fragment or analog thereof, a promoter sequence, e.g., a promoter sequence from an MCH or MCH-R gene or from another gene; an enhancer sequence, e.g., 5' untranslated region (UTR), e.g., a 5' UTR, a 3' UTR; a polyadenylation site; an insulator sequence; or another sequence that modulates the expression of a component of the MCH signaling pathway, e.g., MCH or MCH-R. The cell can then be introduced into the subject.

Primary and secondary cells to be genetically engineered can be obtained form a variety of tissues and include cell types which can be maintained propagated in culture. For example, primary and secondary cells include fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells (myoblasts) and precursors of these somatic cell types. Primary cells are preferably obtained from the individual to whom the genetically engineered primary or secondary cells are administered. However, primary cells may be obtained for a donor (other than the recipient).

The term "primary cell" includes cells present in a suspension of cells isolated from a vertebrate tissue source (prior to their being plated i.e., attached to a tissue culture substrate such as a dish or flask), cells present in an explant derived from tissue, both of the previous types of cells plated for the first time, and cell suspensions derived from these plated cells. The term "secondary cell" or "cell strain" refers to cells at all subsequent steps in culturing. Secondary cells are cell strains which consist of secondary cells which have been passaged one or more times.

Primary or secondary cells of vertebrate, particularly mammalian, origin can be transfected with an exogenous nucleic acid sequence which includes a nucleic acid sequence encoding a signal peptide, and/or a heterologous nucleic acid sequence, e.g., encoding a component of the MCH signaling pathway, e.g., MCH or MCH-R, or an agonist or antagonist thereof, and produce the encoded product stably and reproducibly in vitro and in vivo, over extended periods of time. A heterologous amino acid can also be a regulatory sequence, e.g., a promoter, which causes expression, e.g., inducible expression or upregulation, of an endogenous sequence. An exogenous nucleic acid sequence can be introduced into a primary or secondary cell by homologous recombination as described, for example, in U.S. Pat. No.: 5,641,670, the contents of which are incorporated herein by reference. The transfected primary or secondary cells may also include DNA encoding a selectable marker which confers a selectable phenotype upon them, facilitating their identification and isolation.

Vertebrate tissue can be obtained by standard methods such a punch biopsy or other surgical methods of obtaining a tissue source of the primary cell type of interest. For example, punch biopsy is used to obtain skin as a source of fibroblasts or keratinocytes. A mixture of primary cells is obtained from the tissue, using known methods, such as enzymatic digestion or explanting. If enzymatic digestion is used, enzymes such as collagenase, hyaluronidase, dispase, pronase, trypsin, elastase and chymotrypsin can be used.

The resulting primary cell mixture can be transfected directly or it can be cultured first, removed from the culture plate and resuspended before transfection is carried out. Primary cells or secondary cells are combined with exogenous nucleic acid sequence to, e.g., stably integrate into their genomes, and treated in order to accomplish transfection. As used herein, the term "transfection" includes a variety of techniques for introducing an exogenous nucleic acid into a cell including calcium phosphate or calcium chloride precipitation, microinjection, DEAE-dextrin-mediated transfection, lipofection or electrophoration, all of which are routine in the art.

Transfected primary or secondary cells undergo sufficient number doubling to produce either a clonal cell strain or a heterogeneous cell strain of sufficient size to provide the therapeutic protein to an individual in effective amounts. The number of required cells in a transfected clonal heterogeneous cell strain is variable and depends on a variety of factors, including but not limited to, the use of the transfected cells, the fuictional level of the exogenous DNA in the transfected cells, the site of implantation of the transfected cells (for example, the number of cells that can be used is limited by the anatomical site of implantation), and the age, surface area, and clinical condition of the patient.

The transfected cells, e.g., cells produced as described herein, can be introduced into an individual to whom the product is to be delivered. Various routes of administration and various sites (e.g., renal sub capsular, subcutaneous, central nervous system (including intrathecal), intravascular, intrahepatic, intrasplanchnic, intraperitoneal (including intraomental), intramuscularly implantation) can be used. One implanted in individual, the transfected cells produce the product encoded by the heterologous DNA or are affected by the heterologous DNA itself. For example, an individual who suffers from an antibody-mediated arthritic disorder is a candidate for implantation of cells producing an antagonist of a component of the MCH signaling pathway, e.g., MCH or MCH-R.

An immunosuppressive agent e.g., drug, or antibody, can be administered to a subject at a dosage sufficient to achieve the desired therapeutic effect (e.g., inhibition of rejection of the cells). Dosage ranges for immunosuppressive drugs are known in the art. See, e.g., Freed et al. (1992) N. Engl. J. Med. 327:1549; Spencer et al. (1992) N. Engl. J. Med. 327:1541' Widner et al. (1992) n. Engl. J. Med. 327:1556). Dosage values may vary according to factors such as the disease state, age, sex, and weight of the individual.

Diagnostic Assays

The diagnostic assays described herein involve evaluating level, expression, or activity of a component of the MCH signaling pathway, e.g., MCH or MCH-R, e.g., an MCH-R described herein. Protein levels can be quantitated in a variety of ways well known in the art, such as immunoprecipitation, Western blot analysis (immunoblotting), ELISA or fluorescence-activated cell sorting (FACS). Also, various art-recognized methods are known and/or are commercially available for evaluating insulin secretion from, e.g., a β cell, islet, pancreatic tissue or animal, e.g., a human.

Another method of evaluating MCH signaling in a subject is to determine the presence or absence of a lesion in, or the misexpression of, a gene that encodes a component of the MCH signaling pathway, e.g., MCH or MCH-R, e.g., an MCH-R described herein. The method includes one or more of the following:

detecting, in a tissue of the subject, the presence or absence of a mutation which affects the expression of a gene encoding a component of the MCH signaling pathway, e.g., MCH or MCH-R, or detecting the presence or absence of a mutation in a region which controls the expression of the gene, e.g., a mutation in the 5' control region;

detecting, in a tissue of the subject, the presence or absence of a mutation which alters the structure of a gene encoding a component of the MCH signaling pathway, e.g., MCH or MCH-R;

detecting, in a tissue of the subject, the misexpression of a gene encoding a component of the MCH signaling pathway, e.g., MCH or MCH-R, at the mRNA level, e.g., detecting a non-wild type level of a mRNA;

detecting, in a tissue of the subject, the misexpression of the gene, at the protein level, e.g., detecting a non-wild type level of a component of the MCH signaling pathway, e.g., MCH or MCH-R polypeptide.

In preferred embodiments the method includes: ascertaining the existence of at least one of: a deletion of one or more nucleotides from a gene encoding a component of the MCH signaling pathway, e.g., MCH or MCH-R; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from a gene encoding a component of the MCH signaling pathway, e.g., MCH or MCH-R, or naturally occurring mutants thereof or 5' or 3' flanking sequences naturally associated with the gene; (ii) exposing the probe/primer to nucleic acid of a tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of a gene encoding a component of the MCH signaling pathway, e.g., MCH or MCH-R; the presence of a non-wild type splicing pattern of a messenger RNA transcript of the gene; or a non-wild type level of a gene encoding a component of the MCH signaling pathway, e.g., MCH or MCH-R.

In some embodiments, the method includes determining the structure of a gene encoding a component of the MCH signaling pathway, e.g., MCH or MCH-R, an abnormal structure being indicative of risk for the disorder. In other embodiments, the method includes contacting a sample from the subject with an antibody to a component of the MCH signaling pathway, e.g., MCH or MCH-R, or a nucleic acid which hybridizes specifically with the gene encoding the component of the MCH signaling pathway, e.g., MCH or MCH-R.

Expression Monitoring and Profiling.

The presence, level, or absence of a component of the MCH signaling pathway, e.g., MCH or MCH-R (protein or nucleic acid) in a biological sample can be evaluated by obtaining a biological sample from a test subject and contacting the biological sample with a compound or an agent capable of detecting the protein or nucleic acid (e.g., mRNA, genomic DNA) that encodes a component of the MCH signaling pathway, e.g., MCH or MCH-R, such that the presence of the protein or nucleic acid is detected in the biological sample. The term "biological sample" includes tissues, cells and biological fluids isolated from a subject, as well as tissues, cells and fluids present within a subject, e.g., synovial fluid. Preferred biological samples are serum or synovial fluid. The level of expression of the component of the MCH signaling pathway, e.g., MCH or MCH-R, can be measured in a number of ways, including, but not limited to: measuring the mRNA encoded by the gene; measuring the amount of protein encoded by the gene of; or measuring the activity of the protein encoded by the gene.

The level of mRNA corresponding to a gene encoding a component of the MCH signaling pathway, e.g., MCH or MCH-R, in a cell can be determined both by in situ and by in vitro formats.

Isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length nucleic acid, or a portion thereof, such as an oligonucleotide of at least 7, 15, 30, 50, 100, 250 or 500 nucleotides in length and sufficient to specifically hybridize under stringent conditions to mRNA or genomic DNA of a component of the MCH signaling pathway, e.g., MCH or MCH-R. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the gene of a component of the MCH signaling pathway, e.g., MCH or MCH-R.

The level of mRNA in a sample that is encoded by a gene can be evaluated with nucleic acid amplification, e.g., by rtPCR (Mullis (1987) U.S. Pat. No. 4,683,202), ligase chain reaction (Barany (1991) Proc. Natl. Acad. Sci. USA 88:189-193), self sustained sequence replication (Guatelli et al., (1990) Proc. Natl. Acad. Sci. USA 87:1874-1878), transcriptional amplification system (Kwoh et al., (1989), Proc. Natl. Acad. Sci. USA 86:1173-1177), Q-Beta Replicase (Lizardi et al., (1988) Bio/Technology 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the gene being analyzed.

In another embodiment, the methods further contacting a control sample with a compound or agent capable of detecting mRNA, or genomic DNA of a component of the MCH signaling pathway, e.g., MCH or MCH-R, and comparing the presence of the mRNA or genomic DNA in. the control sample with the presence of mRNA or genomic DNA of a component of the MCH signaling pathway, e.g., MCH or MCH-R, in the test sample. In still another embodiment, serial analysis of gene expression, as described in U.S. Pat. No. 5,695,937, is used to detect transcript levels of a component of the MCH signaling pathway, e.g., MCH or MCH-R, described herein.

A variety of methods can be used to determine the level of protein encoded by a gene of a component of the MCH signaling pathway, e.g., MCH or MCH-R. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect a component of the MCH signaling pathway, e.g., MCH or MCH-R in a biological sample in vitro as well as in vivo. In vitro techniques for detection of a component of the MCH signaling pathway, e.g., MCH or MCH-R, include enzyme linked immunosorbent assays (ELISAs), immunoprecipitations, immunofluorescence, enzyme immunoassay (EIA), radioimmunoassay (RIA), and Western blot analysis. In vivo techniques for detection of a component of the MCH signaling pathway, e.g., MCH or MCH-R, include introducing into a subject a labeled antibody. For example, the antibody can be labeled with a radioactive marker whose presence and location in a subject can be detected by standard imaging techniques. In another embodiment, the sample is labeled, e.g., biotinylated and then contacted to the antibody, e.g., an antibody positioned on an antibody array. The sample can be detected, e.g., with avidin coupled to a fluorescent label.

In another embodiment, the methods further include contacting the control sample with a compound or agent capable of detecting a component of the MCH signaling pathway, e.g., MCH or MCH-R, and comparing the presence of the component protein in the control sample with the presence of the component protein in the test sample.

The invention also includes kits for detecting the presence of a component of the MCH signaling pathway, e.g., MCH or MCH-R, in a biological sample. For example, the kit can include a compound or agent capable of detecting protein (e.g., an antibody) or mRNA (e.g., a nucleic acid probe) of a component of the MCH signaling pathway, e.g., MCH or MCH-R, in a biological sample; and a standard. The compound or agent can be packaged in a suitable container. The kit can further comprise instructions for using the kit to evaluate a subject, e.g., for risk or predisposition to an ocular disorder, e.g., an ocular disorder described herein.

The diagnostic methods described herein can identify subjects having, or at risk of developing, an insulin related disorder, e.g., an insulin related disorder described herein.

The prognostic assays described herein can be used to determine whether a subject can be administered an agent (e.g., an agent that modulates a component of the MCH signaling pathway, e.g., MCH or MCH-R, e.g., an agent described herein) to treat an insulin related disorder, e.g., an insulin related disorder described herein.

All references cited in this application are incorporated herein by reference.

EXAMPLES

Example 1

Production and Analysis of MCH Overexpressing Mice

Production of transgenic animals. Restriction analysis of one $P_1$ clone containing the murine MCH gene allowed for the creation of an unambiguous physical map showing the position and orientation of the MCH-coding region. The clone consists of the expected 16-kb $P_1$ vector and a 72-kb genomic insert. The 70-kb DNA construct used for generation of transgenic mice included approximately 25 kb of 5' and 45 kb of 3' sequence flanking the MCH-coding region.

Fifty-four offspring were obtained from injection of about 200 oocytes, five of which were found to be transgenic by Southern blot analysis. A colony from one of these founders with the highest evident gene copy number (approximately five, with one apparent integration site) was established. The transgene has remained stably integrated and has demonstrated simple Mendelian inheritance. Both heterozygous and homozygous transgenic animals appeared healthy and demonstrated no gross anatomic or behavioral abnormalities.

Overexpression of the MCH transgene. Northern blot analysis performed on hypothalamic tissue of heterozygous transgenic mice showed up to a fourfold difference in MCH mRNA expression between wild-type littermates and transgenic animals in the fed state (data not shown). The average difference between wild-type (n=9) and overexpresser mice (n=8) was almost twofold (45.1±3.0 versus 84.6±3.4 arbitrary units, P<0.0001 by t test). MCH overexpression was confirmed by in situ hybridization histochemistry, which indicated a 50% increase in MCH expression in the fed state. The pattern of distribution of MCH message in the transgenic animals is indistinguishable from that of wild-type mice, as assessed by in situ hybridization studies. No MCH signal could be detected by Northern blot analysis in mRNA from various organs in the periphery including liver, spleen, lung, heart, brown adipose tissue, and white adipose tissue. These data indicate that MCH expression is eutopic in MCH-OE. Immunohistochemical analysis of MCH levels indicated a visually evident increase in MCH immunoreactivity in MCH-OE mice compared with wild type mice.

Body weight, food intake, and percentage of body adiposity. Weight gain of heterozygous and homozygous transgenic mice was studied under several conditions. Heterozygotes fed standard chow or a high-fat diet showed no differences in body weight compared with wild-type littermates. Homozygotes fed standard chow showed a nonsignificant tendency to be heavier than wild-type animals raised under identical conditions. When fed a high-fat diet, however, homozygotes gained significantly more weight than wild-type mice, with a difference of 12.6% by age 13 weeks (P<0.001). The greater body weight of homozygous transgenic mice on a high-fat diet appears to be, at least in part, attributable to increased food intake, as these animals ate about 10% more than wild-typemice (P<0.001). Moreover, these mice were fatter than wild-type mice, as demonstrated by elevated serum leptin concentration (25.6±1.9 vs. 15.0±1.7 ng/ml; P<0.001) and carcass analysis (21.9±1.4 vs. 16.7±1.4% body fat; P=0.02).

Glucose homeostasis. Mean blood glucose determined at the end of the light cycle (e.g., preprandial) for homozygous transgenic mice compared with wild-type mice was 181±4 versus 161±5 mg/dl (P=0.003), respectively. Transgenic mice also had higher mean blood glucose measured for 2 hours after intraperitoneal glucose injection than wild-type mice (369±19 vs. 296±14 mg/dl; P=0.002). Mean plasma insulin concentration determined at the beginning of the light cycle (e.g., postprandial) was dramatically higher in the homozygous transgenic compared with wild-type animals (9.5±1.7 vs. 1.0±0.2 ng/ml; P<0.001). Fifteen minutes after injection of insulin, mean blood glucose decreased by only 5% in the homozygous transgenics compared with 31% in the wild-type mice (difference between groups for blood glucose response: P<0.001). Finally, pancreatic islet histology of transgenic mice demonstrated marked increase in islet size.

Example 2

MCH Stimulation Of Insulin Secretion

MCH stimulation of overnight cultured islets isolated from C57B1/6J mice showed a concentration- and time-dependent insulin secretion. A 2.4-fold stimulation was observed at 100 nM after 30 min incubation in the presence of 11.1 mM glucose (Control 0.86±0.22 vs MCH 2.1±0.11% of insulin content, n=3, p<0.02). A similar stimulatory effect was evident when a mouse clonal β-cell line (βTC3) was treated with MCH, showing a direct effect of the peptide on the β-cells. MCH treatment of islets isolated from MCH over expressing mice showed a 4-fold stimulatory response (Control 2.8±0.36 vs 11.4±0.49 pg/μg protein, n=2) showing an enhanced effect of MCH in the presence of hyperinsulinemia.

Example 3

Expression of MCH and MCH Receptor in Islets

Using immunohistochemistry, it has been found that MCH is present in the islet.

To evaluate whether MCH stimulated insulin secretion via its receptor, RNA was prepared from mouse islets and the clonal β-cells and MCH receptor expression levels were examined using Taqman analysis. Independent experiments showed the presence of MCH receptor (MCHR1) expression in the islets and in the clonal β-cells using the hypothalamus as a positive control. MCH receptor expression levels were 9-fold lower in the islets (Hypothalamus 919.0 vs Islet 100.0 arbitrary units) and 12-fold lower in the β-cell lines (Hypothalamus 7771.0 vs β-cells 633.5 arbitrary units) compared to the levels in the hypothalamus. These data indicate that MCH stimulates insulin release from the islets/β-cells via its own receptor.

To begin to examine the mechanism of action of MCH in the islets the effect of the peptide on MAP kinase activity was investigated. No consistent effect could be detected in MAP kinase levels in islets or clonal β-cells treated with 1 μM MCH indicating a MAPK-independent effect.

Taken together these data suggest that MCH directly stimulates insulin secretion and provides a novel system to study MCH signaling pathways.

We claim:

1. A method of promoting β cell function or development, selected from the group consisting of increasing insulin secretion, β cell size, and β beta cell growth the method comprising contacting a β cell with an effective amount of an agonist of melanocyte concentrating hormone (MCH), wherein the agonist comprises MCH or a peptide analog of MCH comprising the sequence VYRPC (amino acids 12-16 of SEQ ID NO:1), wherein the agonist has MCH activity in a fish skin teleost bioassay.

2. The method of claim 1, wherein the agonist is contacted with the β cell in vitro.

3. The method of claim 2, further comprising implanting the cell into a subject.

4. The method of claim 3, wherein the subject is a living mammal.

5. The method of claim 4, wherein the mammal is a human.

6. The method of claim 4, wherein the mammal is at risk for or has an insulin related disorder.

7. The method of claim 3, wherein the subject is a non-human animal.

8. The method of claim 7, wherein the animal is an animal model of an insulin related disorder.

9. The method of claim 2, wherein the β cell is in an isolated pancreatic tissue.

10. The method of claim 9, wherein the isolated pancreatic tissue comprises an islet or islet equivalent.

11. The method of claim 2, wherein the β cell is autologous to the subject.

12. The method of claim 2, wherein the agonist is contacted with the β cell in vivo.

13. The method of claim 2, wherein the β cell is in a living mammal.

14. The method of claim 13, wherein the mammal is a human.

15. The method of claim 12, wherein the mammal is at risk for or has an insulin related disorder.

16. The method of claim 12, wherein the β cell is in a non-human animal.

17. The method of claim 16, wherein the animal is an animal model of an insulin related disorder.

* * * * *